United States Patent
Lal et al.

[11] Patent Number: 5,954,702
[45] Date of Patent: Sep. 21, 1999

[54] INTERFACE GEOMETRY FOR ADHESIVE BONDS

[75] Inventors: Birendra K. Lal, Lake Zurich; Donna L. Rostron, Bartlett, both of Ill.; JoAnn DeMarco, Westerfield, Conn.

[73] Assignee: Baxter International Inc., Deerfield, Ill.

[21] Appl. No.: 08/642,281

[22] Filed: May 3, 1996

[51] Int. Cl.⁶ .................................................. A61M 25/00
[52] U.S. Cl. ........................... 604/283; 604/905; 128/912
[58] Field of Search ............................ 604/280.283, 905; 128/912, DIG. 26

[56] References Cited

U.S. PATENT DOCUMENTS

| | | |
|---|---|---|
| 813,918 | 2/1906 | Schmitz . |
| 2,551,710 | 5/1951 | Slaughter . |
| 3,157,724 | 11/1964 | Salyer et al. . |
| 3,218,380 | 11/1965 | Euling et al. . |
| 3,260,776 | 7/1966 | Lindstrom, Jr. et al. . |
| 3,581,776 | 6/1971 | Sheahan . |
| 3,775,523 | 11/1973 | Haley . |
| 3,856,889 | 12/1974 | McConnell . |
| 3,886,227 | 5/1975 | VanBrederode et al. . |
| 3,974,240 | 8/1976 | Bock et al. . |
| 4,014,369 | 3/1977 | Kobres, Jr. . |
| 4,157,194 | 6/1979 | Takahashi . |
| 4,157,235 | 6/1979 | Lagabe et al. . |
| 4,193,899 | 3/1980 | Brenner et al. . |
| 4,374,882 | 2/1983 | Harlan . |
| 4,422,999 | 12/1983 | Mitchell . |
| 4,444,817 | 4/1984 | Subramanian . |
| 4,613,533 | 9/1986 | Loomis et al. . |
| 4,623,567 | 11/1986 | Hert . |
| 4,678,834 | 7/1987 | Boivin et al. . |
| 4,698,196 | 10/1987 | Fabian . |
| 4,721,637 | 1/1988 | Suzuki . |
| 4,737,547 | 4/1988 | White . |
| 4,826,477 | 5/1989 | Adams ..................................... 604/283 |
| 4,875,468 | 10/1989 | Krauter et al. ........................... 604/283 |
| 4,886,634 | 12/1989 | Strutzel et al. . |

(List continued on next page.)

FOREIGN PATENT DOCUMENTS

| | | |
|---|---|---|
| 250874 | 8/1988 | Czechoslovakia . |
| 0 133 355 | 7/1984 | European Pat. Off. . |
| 0 256 644 | 2/1988 | European Pat. Off. . |
| 0 450 088 A1 | 10/1991 | European Pat. Off. . |
| 0450330 | 10/1991 | European Pat. Off. ............... 604/283 |
| 4-332624 | 11/1992 | Japan . |
| 5-017639 | 1/1993 | Japan . |
| 7-205275 | 8/1995 | Japan . |
| 7-205276 | 8/1995 | Japan . |
| WO 80/02671 | 11/1980 | WIPO . |
| WO 92/18173 | 10/1992 | WIPO . |
| WO 94/26793 | 11/1994 | WIPO . |
| WO 96/36374 | 11/1996 | WIPO . |
| 97/07032 | 4/1997 | WIPO . |
| 97/07033 PCT/US | 4/1997 | WIPO . |
| 97/07034 PCT/US | 4/1997 | WIPO . |
| 97/07040 | 4/1997 | WIPO . |
| WO 9608520 | 4/1997 | WIPO . |

OTHER PUBLICATIONS

European Plastic News, Jun. 1996; *Medical Tubes Use Metallocene Resin*, p. 17.

Industrial & Production Engineering (PE), Dec. 1988, *Extrusion Line for Medical Tubes*, p. 17.

(List continued on next page.)

*Primary Examiner*—Mark Bockelman
*Assistant Examiner*—Jennifer R. Sadula
*Attorney, Agent, or Firm*—Mark J. Buonaiuto; Joseph A. Fuchs

[57] ABSTRACT

The present invention provides a housing for use in the administration of medical fluids comprising a body having an opening at a distal end to a chamber, the chamber is connected to an interior flow channel, and a plurality of ribs are positioned in the chamber and are circumferentially spaced, the ribs are positioned inward of the body opening.

35 Claims, 2 Drawing Sheets

U.S. PATENT DOCUMENTS

| | | |
|---|---|---|
| 4,906,496 | 3/1990 | Hosono et al. . |
| 4,948,643 | 8/1990 | Mueller . |
| 4,957,974 | 9/1990 | Ilenda et al. . |
| 5,018,945 | 5/1991 | D'Silva . |
| 5,045,620 | 9/1991 | Itaba et al. . |
| 5,048,572 | 9/1991 | Levine . |
| 5,151,019 | 9/1992 | Danby . |
| 5,169,708 | 12/1992 | Amaral et al. . |
| 5,205,821 | 4/1993 | Kruger et al. ............ 604/283 |
| 5,225,451 | 7/1993 | Rogers et al. . |
| 5,241,031 | 8/1993 | Mehta . |
| 5,263,945 | 11/1993 | Byrnes et al. ............ 604/283 |
| 5,264,488 | 11/1993 | Takeuchi et al. . |
| 5,274,035 | 12/1993 | Chundury . |
| 5,281,670 | 1/1994 | Lee et al. . |
| 5,343,738 | 9/1994 | Skaggs . |
| 5,380,301 | 1/1995 | Prichard et al. ........ 604/283 |
| 5,439,454 | 8/1995 | Lo et al. . |
| 5,525,388 | 6/1996 | Wand et al. . |
| 5,562,127 | 10/1996 | Fanselow et al. . |
| 5,573,822 | 11/1996 | Nishikawa . |
| 5,620,760 | 4/1997 | Galimberti . |
| 5,624,402 | 4/1997 | Imbert ...................... 604/283 |
| 5,629,059 | 5/1997 | Desai et al. . |
| 5,632,735 | 5/1997 | Wyatt et al. ............ 604/283 |
| 5,638,660 | 6/1997 | Kuo . |

OTHER PUBLICATIONS

*Functionalized Modified High Melt Flow Polyolefins*, Wilpers et al., United States Statutory Invention Registration No. H1419.

*The Effect of Plastic Formulation Variables on Bond Strengths Achieved With Typical Medical Device Adhesives*, presented at Manufacturing Medical Plastics '95 by Pat Courtney, Senior Application Engineer, Loctite Corporation.

Patrick J. Courtney and James Serenson, "Adhesive Bonding of Medical Plastics: An Overview", Jan./Feb. 1996 Medical Plastics and Biomaterials, pp. 20–25.

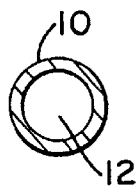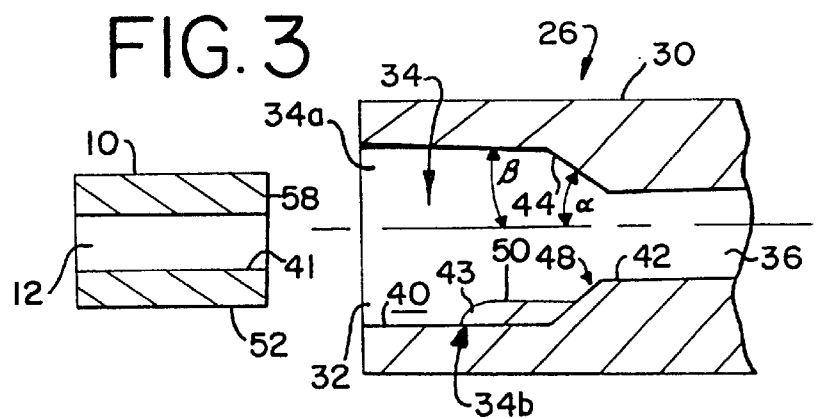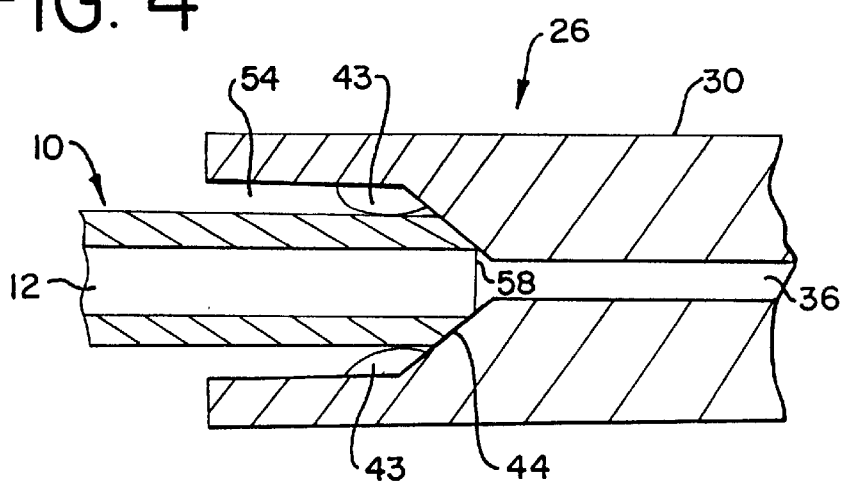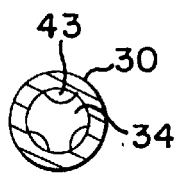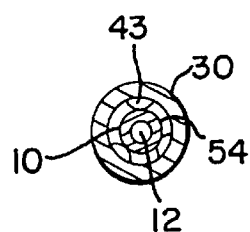

INTERFACE GEOMETRY FOR ADHESIVE BONDS

TECHNICAL FIELD

This invention relates to a rigid medical housing for use in fluid administration sets and more specifically, to a modified housing sleeve having circumferentially spaced ribs positioned inward of a housing opening for centering tubing within the housing.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubings must have a unique combination of properties, so that the tubing may be used in fluid administration sets. Among these are the materials must be optically clear, environmentally compatible, have sufficient yield strength and flexibility, have a low quantity of low molecular weight additives, and be compatible with medical solutions.

It is desirable for medical tubing to be optically transparent to allow for visual inspection of fluids in the tubing.

It is also a requirement that the tubing materials be environmentally compatible as a great deal of medical tubing is disposed of in landfills and through incineration. Further benefits are realized by using a material which is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration, causing corrosion of the incinerator and possible pollution to the environment.

To be compatible with medical solutions, it is desirable that the tubing material be free from or have a minimal content of low molecular weight additives such as plasticizers, stabilizers and the like. These components could be extracted into the therapeutic solutions that come into contact with the material. The additives may react with the therapeutic agents or otherwise render the solution ineffective. This is especially troublesome in bio-tech drug formulations where the concentration of the drug is measured in parts per million (ppm), rather than in weight or volume percentages. Even minuscule losses of the bio-tech drug can render the formulation unusable. Because bio-tech formulations can cost several thousand dollars per dose, it is imperative that the dosage not be changed.

Polyvinyl chloride ("PVC") has been widely used to fabricate medical tubings as it meets most of these requirements. However, because PVC by itself is a rigid polymer, low molecular weight components known as plasticizers must be added to render PVC flexible. As set forth above, these plasticizers may leach out of the tubing and into the fluid passing through the tubing to contaminate the fluid or to render the fluid unusable. For this reason, and because of the difficulties encountered in incinerating PVC, there is a need to replace PVC medical tubing.

Polyolefins have been developed which meet many of the requirements of medical containers and tubing, without the disadvantages associated with PVC. Polyolefins typically are compatible with medical applications because they have minimal extractability to the fluids and contents which they contact. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

For example, because of the inert nature of polyolefins, due in part to the non-polar nature of the polymer, difficulties have been encountered in bonding the polyolefin materials to polar molecules, such as polycarbonates, ABS and acrylic polymers. Typically, medical containers such as I.V. bags are connected to a patient through a series of connected tubing that have drip chambers, Y-type injection sites, venous catheters and the like between the bag and the patient. Many of these components include rigid housings manufactured from polymers such as polycarbonates, acrylics, ABS and copolyesters. The housings have sleeves in which the tubing is inserted in a telescoping fashion to attach the tube to the housing. Therefore, it is necessary for the medical tubing to be connected to the rigid housing to form a fluid tight seal with the housings.

PVC tubing is typically secured within such housings using solvent bonding techniques. Solvent bonding requires exposing the end of the tubing to be inserted into the housing to a solvent such as cyclohexanone or methyl ethyl ketone. The solvent effectively softens or "melts" the PVC so when the tubing is inserted into the housing, a bond is formed. It is desirable that the outer tubing diameter be approximately the same dimension or slightly larger than the inner diameter of the housing to form an interference fit, as close tolerances in these dimensions assists in forming a secure bond.

Solvent bonding techniques, however, are ineffective on certain polyolefins including polyethylene. Problems have also been encountered in using adhesive bonding techniques.

One attempt at overcoming this problem was to use a two step process of applying a primer material to the surface to be bonded followed by an adhesive. Cyanoacrylate adhesives have worked with some success using this technique with a primer. However, the two step process adds an additional step to a manufacturing process which could slow down the production line and increase the labor costs. Further, primers increase the cost of the process. Third, because primers typically contain large quantities of volatile chemicals such as organic solvents, and might lead to toxicity, safety and environmental problems. Fourth, primers may limit manufacturing options as they have a limited on-part life time, i.e., the primers will lose their activities within hours after exposure to an ambient environment.

The present invention solves these and other problems.

DISCLOSURE OF INVENTION

The present invention provides a housing for use in the administration of medical fluids. The housing comprises a body having an opening at a distal end to a chamber, the chamber is connected to an interior flow channel, and a plurality of ribs are positioned in the chamber and are circumferentially spaced. The ribs are positioned inward of the body opening to minimize scraping off of adhesive from tubing inserted therein.

Preferably there are at least three ribs, and more preferably five ribs, that serve to center medical tubing within the housing and to create an adhesive area between a tubing outer diameter and an inner diameter of the housing chamber. It is also preferred that the ribs have a radiused outer profile. The ribs may be spaced apart at an equal or unequal distance, and may haves equal or unequal lengths.

Preferably the chamber is generally funnel shaped having walls that gently diametrically taper inwardly and has a section that tapers more drastically inward to connect the chamber to a smaller diameter fluid flow channel. The more drastic taper will also provide a stop that prevents the tubing and adhesive from entering the fluid flow path.

The present invention further provides a method for attaching medical tubing to a medical housing.

BRIEF DESCRIPTION OF DRAWINGS

FIG. 1 is an enlarged cross-sectional view of a medical tubing;

FIG. 3 is a side elevation view in section of a tubing and housing assembly prior to insertion of the tubing into the housing;

FIG. 4 is a side elevation view in section of a tubing and housing assembly with the tubing inserted into the housing;

FIG. 4A is a side elevation view in section of a tubing and housing assembly with the tubing inserted into the housing having ribs of different length;

FIG. 5 is an end view of a housing sleeve;

FIG. 5A is an end view of a housing sleeve having ribs spaced unequal distances apart from each other; and, FIG. 6 is an end view of a housing sleeve with a tubing inserted therein.

BEST MODE FOR CARRYING OUT THE INVENTION

Figure 2:
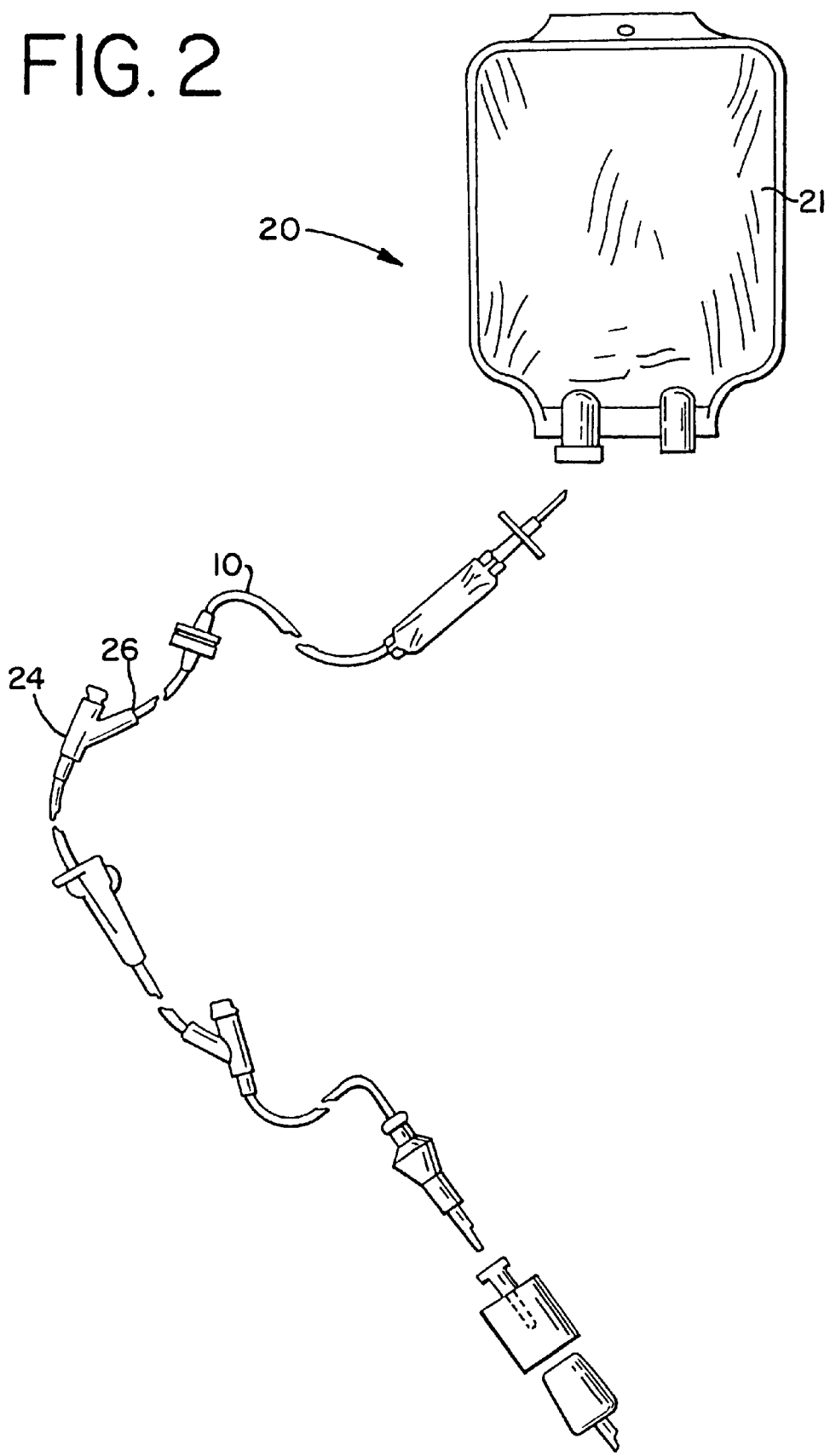
FIG. 2 is a schematic view of gravity pressurized fluid administration set.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

I. Polymer Blends

The polymer blends of the present invention include polyethylene copolymers and an additive. The. polyethylene copolymers are selected from the group of ethylene copolymerized with comonomers selected from alpha-olefins such as butene-1 or octene-1. These copolymers shall be referred to as ultra-low density polyethylenes. The preferred additive may be selected from the group consisting of polyoxyethylene(5)oleylamine (Ethomeen 0/15, Akzo Nobel Chemical Company), bis(2-hydroxyethyl)soyaamine (Ethomeen S/12), bis(2-hydroxyethyl)oleylamine (Ethomeen 0/12), and polyoxyethylene(5)octadecylamine (Ethomeen 18/15). The polymer blends are capable of being fabricated into medical tubing and attached to rigid polymers using cyanoacrylate adhesives.

The blends should have the polyethylene copolymer in an amount by weight within the range of 90%–99.999%, more preferably 98.0%–99.99%. The additive should be in an amount by weight within the range of 0.001%–10%, and more preferably 0.01%–2%.

The components of the polymer blends should be blended through molten mixing, physical blending or the like.

II. Method of Fabricating Medical Tubing

FIG. 1 shows medical tubing 10 of the present invention fabricated from one of the blends of the present invention and having a fluid passageway 12. The medical tubing 10 is preferably fabricated by an extrusion process.

III. Rigid Medical Housings

The administration set 20 in FIG. 2 includes tubing 10 connected to a fluid or I.V. container 21 which is in fluid communication with various rigid plastic housings such as Y-type injection sites 24 through tubing 10. The tubing 10 connects to a housing sleeve 26 on the housing 24.

The housing 24 and its housing sleeve 26 is preferably constructed of a rigid polymer such as polycarbonates, copolyesters, acrylics, ABS, nylon, polystyrene, polypropylene, polyethylene, polysulfone, and polyimide. The term "Rigid polymers" are those having a modulus of elasticity of greater than 50,000 psi and preferably greater than 100,000 psi. Typically, the housings are constructed using injection molding techniques.

As shown in FIGS. 3 and 4, it is preferred that housing sleeve 26 have a generally elongate cylindrical body 30 having an opening 32 at its distal end. The opening 32 leads to a chamber 34 which is dimensioned to receive an end portion of the tubing 10. The housing chamber 34 is connected to an interior fluid flow channel 36.

Referring again to FIG. 3, the housing sleeve 26 has an inner surface 40 which defines a generally funnel-shaped chamber 34. The chamber 34 has a first area 34$a$ proximate the opening 32 and having a first diameter, and a second area 34$b$ where a plurality of ribs 43 are positioned. The interior flow channel 36 preferably has a second diameter which is less than the first diameter. A taper 44 connects the second area 34$b$ to the interior flow channel 36. The degree $\alpha$ of taper 44 preferably is within the range of 0.25–1.0 degrees as measured from a centerline 46 of the housing sleeve 26.

Preferably, the first and second chamber areas 34$a$ and 34$b$ first diameter gently tapers or decreases diameter from the opening 32 to the flow channel 36. This taper is known as the draft angle $\beta$ as measured from the centerline 46. Because the housing is typically fabricated using an injection molding process, the chamber is formed by a tool whose shape defines the chamber 34. The tool must be removed after fabricating the housing and the draft angle $\beta$ of the interior surface 40 assists in removing the tool.

It is desirable that the second diameter of the flow channel 36 be less than that of the outer diameter of the flexible tubing 10 so that a portion of the taper 44 may serve as a stop 48 to prevent further insertion of the tubing 10 into the housing sleeve 26 and to prevent the migration of adhesive into the fluid path. (See also FIG. 4). Also, it is preferable that the tubing 10 fluid passageway 12 be in alignment with the housing sleeve 26 flow channel 36 and that an inner tubing wall 41 should be in alignment with an inner wall 42 of the flow channel 36 to minimize the resistance to fluid flow at the juncture. In effect, the taper 44 defines a recess where the tubing fits into to achieve this desirable alignment.

As shown in FIGS. 3–6, there is a plurality of circumferentially spaced ribs 43 positioned in area 34$b$. As shown in FIG. 5, preferably there are at least three ribs 43 spaced apart about 120°. More preferably there are five ribs. Of course the ribs 43 could also be unevenly spaced without departing from the present invention. There may also be any number of ribs 43 greater than three. The ribs 43 extend from the inner diameter surface 40 in the second chamber area 34b and preferably terminate at some point prior to the fluid channel 36. The ribs 43 may be of varying lengths from one another and each may start and stop at different locations within area 34b. Preferably, a portion of the ribs 43 outer surface 50 extends parallel to the housing centerline 46.

The ribs 43 have a height measured from the interior surface 40 to a highest point of the rib 43 ranging from about 0.001 inches to about 0.010 inches. The height of the ribs 43 provides the desired circumferential clearance between an outer surface 52 of the tubing 10 and the outer portions the ribs 43 to define an adhesive area 54. The adhesive area 54 should be large enough to accommodate a sufficient quantity of adhesive to create a secure adhesive bond, but not so large as to risk creating a leak or a poor bond between the tubing 10 and the housing sleeve 26.

The height of the ribs 43, and their position inward of the opening 32 minimizes interference and scraping off of adhesive from the outer surface 52 of the tubing 10 upon insertion of the tubing 10 into the chamber 34. The ribs 43 can have any geometric profile, but are preferably radiused, or slightly rounded, again so that the ribs 43 minimally interfere with the adhesive. If a significant amount of adhesive is removed during insertion of the flexible tubing 10, channels could form between the tubing 10 and the housing sleeve 26, allowing for undesirable leakage of the fluid being transferred through the tubing 10.

The ribs 43 also serve as a guiding means that assists in centering the tubing 10 within the housing sleeve 26. Centering the tubing 10 within the housing sleeve 26 is important for providing equal circumferential distribution of the adhesive between the tubing 10 and housing sleeve 26, and providing for a more reliable adhesive bond.

FIG. 4 shows the tubing 10 connected to the housing sleeve 26 to define a housing and tubing assembly 56. Tubing 10 is positioned in the chamber 34 of the housing sleeve 26 such that a tubing end 58 abuts the stop 48. The adhesive area 54 is shown filled with an adhesive.

The present invention further provides a method of forming the tubing and housing assembly 56 comprising the steps of providing a rigid housing sleeve 26 having an opening 32, leading to a chamber 34 which in turn connects to an interior channel 36. A plurality of circumferentially spaced ribs 43 as described above are positioned in the chamber 34. The method further includes the step of applying a quantity of adhesive to the adhesive area 54, inserting the end portion of the tubing 10 into the sleeve opening 32 until the tubing end 58 contacts the stop 48. More preferably the tubing 10 is inserted into the chamber 34 and the adhesive is then added to the adhesive area 54 and allowed to wick about the circumference of the tubing. The ribs 43 guide the end portion 58 of the tubing 10 into a central portion of the housing sleeve 26 thereby defining the boundaries of the adhesive area 54 between the outer surface of the tube 52 and the inner surface 40 of the housing sleeve 26. The method finally includes the step of hardening the adhesive forming a bond in the adhesive area 54 to secure the tube 10 within the housing sleeve 26.

Suitable adhesives for use in the above method include the family of cyanoacrylate adhesives.

While specific embodiments have been illustrated and described, numerous modifications are possible without departing from the spirit of the invention, and the scope of protection is only limited by the scope of the accompanying claims.

We claim:

1. A housing for use in the administration of medical fluids comprising:

a body having an opening at a distal end, an interior chamber and an interior flow channel, one end of the chamber being adjacent the body opening and another end of the chamber being connected to the interior flow channel; and, a plurality of ribs are positioned in the chamber and are circumferentially spaced, the ribs are positioned inward of the body opening and the ribs have an outer portion for guiding an outer surface of an inserted tubing into the chamber.

2. The housing of claim 1 wherein the chamber is generally funnel-shaped.

3. The housing of claim 2 wherein the ribs extend from a generally flat area inward of the body opening to a position outward of the interior flow channel.

4. The housing of claim 2 wherein the ribs have a radiussed outer profile.

5. The housing of claim 1 wherein the ribs are spaced about equidistant from one another.

6. The housing of claim 1 wherein at least two adjacent ribs are spaced an unequal distance from each other as compared to a distance between other adjacent ribs.

7. The housing of claim 1 wherein the chamber has a first area proximate the opening, the first area has a first diameter, a second area inward of the first area where the ribs are positioned, wherein the flow channel has a second diameter less than the first diameter, and a tapered area connects the flow channel to the second area.

8. The housing of claim 1 wherein each of the ribs have a length dimension and wherein the length dimension of each of the ribs is about the same.

9. The housing of claim 1 wherein each of the ribs have a length dimension and wherein the length dimension of at least one of the ribs differs from the length dimension of another rib.

10. The housing of claim 1 wherein there are greater than 3 ribs.

11. The housing of claim 1 wherein the ribs guide the tubing into a substantially center portion of the chamber.

12. A housing and tubing assembly for use in administration of medical fluids, the assembly comprising:

a flexible tubing having an inner and outer diameter;

a rigid plastic housing sleeve, the housing sleeve including an elongate body having an opening at a distal end, an interior chamber and an interior fluid flow channel, one end of the chamber being adjacent the body opening and another end of the chamber being connected to the interior flow channel, a plurality of spaced ribs are positioned in the chamber inward from the opening for guiding the outer diameter of the tubing into the chamber; and, wherein a portion of the tubing is secured within the chamber.

13. The assembly of claim 12 wherein the tubing is secured to the body with an adhesive bond.

14. The tubing assembly of claim 13 wherein the ribs have a height sufficient for centering the flexible tubing within the chamber.

15. The tubing assembly of claim 13 wherein the ribs have a radiused outer profile.

16. The assembly of claim 12 wherein the chamber has a first area having a first diameter proximate the opening, a second area inward of the first area, the ribs being positioned in the second area, wherein the flow channel has a diameter less than the first diameter of the first area, and a tapered area connects the flow channel to the second area.

17. The tubing assembly of claim 16 wherein the ribs are positioned inward of the opening but outward of the interior flow channel.

18. The tubing assembly of claim 12 wherein the tubing is centrally disposed within the chamber providing equal clearance circumferentially therebetween.

19. The tubing assembly of claim 12 wherein an outer diameter surface dimension of the flexible tubing is greater than an inner diameter surface dimension of a portion of the interior fluid flow channel to define a stop.

20. The tubing assembly of claim 12 wherein the ribs are spaced about equidistant from one another.

21. The housing of claim 12 wherein at least two adjacent ribs are spaced a distance from each other that is different than a spacing between other adjacent ribs.

22. The housing of claim 12 wherein each of the ribs have a length dimension and wherein the length dimension of each of the ribs is about the same.

23. The housing of claim 12 wherein each of the ribs have a length dimension and wherein the length dimension of at least one of the ribs differs from the length dimension of another rib.

24. A housing and tubing assembly for use in administration of medical fluids, the assembly comprising:

a flexible tubing having an inner and an outer diameter;

a rigid plastic housing sleeve, the housing sleeve including an elongate body having an opening at a distal end, an interior chamber and an interior fluid flow channel, one end of the chamber being adjacent the body opening and another end of the chamber being connected to the interior flow channel, a plurality of spaced ribs are positioned in the chamber inward from the opening for guiding the outer diameter of the tubing into the chamber and for centering the tubing in the chamber, the ribs providing a circumferential clearance between the outer diameter of the tubing and the interior chamber of the housing sleeve to define an adhesive area; and, wherein a portion of the tubing is secured within the chamber with an adhesive bond.

25. The assembly of claim 24 wherein the chamber has a first area having a first diameter proximate the opening, a second area inward of the first area, the ribs being positioned in the second area, wherein the flow channel has a diameter less than the first diameter of the first area, and a tapered area connects the flow channel to the second area.

26. The assembly of claim 24 wherein an outer diameter surface dimension of the flexible tubing is greater than an inner diameter surface dimension of a portion of the interior fluid flow channel to define a stop.

27. The assembly of claim 24 wherein the ribs have a radiused outer profile.

28. The assembly of claim 24 wherein the ribs are spaced about equidistant from one another.

29. The assembly of claim 24 wherein at least two adjacent ribs are spaced a distance from each other that is different than a spacing between other adjacent ribs.

30. The assembly of claim 24 wherein the ribs are positioned inward of the opening but outward of the interior flow channel.

31. The assembly of claim 24 wherein each of the ribs have a length dimension and wherein the length dimension of each of the ribs is about the same.

32. The assembly of claim 24 wherein each of the ribs have a length dimension and wherein the length dimension of at least one of the ribs differs from the length dimension of another rib.

33. The assembly of claim 24 wherein the ribs have an outer portion and wherein the outer portion of the ribs contacts the outer surface of the tubing.

34. A housing and tubing assembly for use in administration of medical fluids, the assembly comprising:

a flexible tubing having substantially fixed inner and outer diameters;

a rigid plastic housing sleeve, the housing sleeve including an elongate body having an opening at a distal end, an interior chamber and an interior fluid flow channel, one end of the chamber being adjacent the body opening and another end of the chamber being connected to the interior flow channel, a plurality of spaced ribs are positioned in the chamber inward from the opening for guiding the outer diameter of the tubing into the chamber and for centering the tubing in the chamber, the ribs providing a circumferential clearance between the outer diameter of the tubing and the interior chamber of the housing sleeve to define an adhesive area;

wherein a portion of the tubing extends beyond the ribs and abuts a stop; and, wherein a portion of the tubing is secured within the chamber with an adhesive bond.

35. The assembly of claim 34 wherein the ribs have an outer portion and wherein the outer portion of the ribs contacts the outer surface of the tubing.

* * * * *

UNITED STATES PATENT AND TRADEMARK OFFICE
CERTIFICATE OF CORRECTION

PATENT NO. : 5,954,702
DATED : September 21, 1999
INVENTOR(S) : Lal et al.

It is certified that error appears in the above-identified patent and that said Letters Patent is hereby corrected as shown below:

Under Assignee, please add --Loctite Corporation, Hartford, CT--.

Signed and Sealed this

Nineteenth Day of June, 2001

*Attest:*

NICHOLAS P. GODICI
*Attesting Officer*    *Acting Director of the United States Patent and Trademark Office*